(12) United States Patent
Podhajsky

(10) Patent No.: US 8,463,396 B2
(45) Date of Patent: *Jun. 11, 2013

(54) POWER-STAGE ANTENNA INTEGRATED SYSTEM WITH HIGH-STRENGTH SHAFT

(75) Inventor: Ronald J. Podhajsky, Boulder, CO (US)

(73) Assignee: Covidien LLP, Mansfield, MA (US)

( * ) Notice: Subject to any disclaimer, the term of this patent is extended or adjusted under 35 U.S.C. 154(b) by 1071 days.

This patent is subject to a terminal disclaimer.

(21) Appl. No.: 12/436,239

(22) Filed: May 6, 2009

(65) Prior Publication Data
US 2010/0286683 A1 Nov. 11, 2010

(51) Int. Cl.
*A61B 18/18* (2006.01)
*A61B 18/04* (2006.01)
*A61N 1/00* (2006.01)

(52) U.S. Cl.
USPC .............................. 607/101; 607/156; 606/33

(58) Field of Classification Search
USPC .................... 607/100–102, 154, 156; 606/27, 606/33–34, 41, 45–50
See application file for complete search history.

(56) References Cited

U.S. PATENT DOCUMENTS

| | | | |
|---|---|---|---|
| 3,631,363 A | 12/1971 | Miller | |
| 4,028,518 A | 6/1977 | Boudouris et al. | |
| 4,397,313 A | 8/1983 | Vaguine | |
| 4,462,412 A | 7/1984 | Turner | |
| 4,572,190 A | 2/1986 | Azam et al. | |
| 4,798,215 A | 1/1989 | Turner | |
| 5,097,844 A | 3/1992 | Turner | |
| 5,417,210 A | 5/1995 | Funda et al. | |
| 5,445,635 A | 8/1995 | Denen et al. | |
| 6,031,375 A | 2/2000 | Atalar et al. | |
| 6,071,281 A | 6/2000 | Burnside et al. | |
| 6,123,702 A | 9/2000 | Swanson et al. | |
| 6,245,065 B1 | 6/2001 | Panescu et al. | |
| 6,293,941 B1 | 9/2001 | Strul et al. | |

(Continued)

FOREIGN PATENT DOCUMENTS

| | | |
|---|---|---|
| DE | 390937 | 3/1924 |
| DE | 1099658 | 2/1961 |

(Continued)

OTHER PUBLICATIONS

International Search Report PCT/US2010/032796 dated Jul. 19, 2010.

(Continued)

*Primary Examiner* — Linda Dvorak
*Assistant Examiner* — Adam Avigan

(57) ABSTRACT

Disclosed is a microwave antenna assembly that includes proximal and distal radiating sections and a junction member. The proximal radiating section includes inner and outer conductors and DC power and neutral conductors. The inner conductor is disposed within the outer conductor and the DC power and neutral conductors are disposed radially outward therefrom. The junction member mates the distal and proximal radiating sections such that the distal and proximal radiating sections are positioned relative to one another. The junction member further includes a microwave signal amplifier (MSA) that receives a signal at a first energy level from the inner and outer conductors and a DC power signal from the DC power and neutral conductors. The MSA amplifies the signal from the first energy level to an additional, greater energy level. The junction member provides the microwave signal at the additional energy level to the proximal and distal radiating sections.

10 Claims, 12 Drawing Sheets

U.S. PATENT DOCUMENTS

| | | | |
|---|---|---|---|
| 6,375,606 | B1 | 4/2002 | Garibaldi et al. |
| 6,380,815 | B1 | 4/2002 | Fehrenbach et al. |
| 6,494,880 | B1 | 12/2002 | Swanson et al. |
| 6,603,994 | B2 | 8/2003 | Wallace et al. |
| 6,725,080 | B2 | 4/2004 | Melkent et al. |
| 6,771,139 | B2 | 8/2004 | Schultheiss et al. |
| 6,786,905 | B2 | 9/2004 | Swanson et al. |
| 6,878,147 | B2 * | 4/2005 | Prakash et al. .................. 606/33 |
| 6,989,010 | B2 | 1/2006 | Francischelli et al. |
| 7,439,736 | B2 | 10/2008 | Meaney et al. |
| 7,467,015 | B2 | 12/2008 | Van der Weide |
| 7,565,207 | B2 | 7/2009 | Turner et al. |
| 8,216,227 | B2 * | 7/2012 | Podhajsky ...................... 606/41 |
| 2002/0022836 | A1 | 2/2002 | Goble et al. |
| 2003/0199863 | A1 | 10/2003 | Swanson et al. |
| 2004/0097805 | A1 | 5/2004 | Verard et al. |
| 2004/0242992 | A1 | 12/2004 | Hareyama |
| 2005/0101947 | A1 | 5/2005 | Jarrard et al. |
| 2006/0030914 | A1 | 2/2006 | Eggers et al. |
| 2007/0260235 | A1 | 11/2007 | Podhajsky |
| 2010/0036369 | A1 * | 2/2010 | Hancock ........................ 606/33 |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 159 926 | 5/2001 |
| EP | 1 278 007 | 1/2003 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO97/41924 | 11/1997 |
| WO | WO97/43971 | 11/1997 |
| WO | WO00/48672 | 8/2000 |
| WO | WO00/51513 | 9/2000 |
| WO | WO01/01847 | 1/2001 |
| WO | WO01/74252 | 10/2001 |
| WO | WO02/45790 | 6/2002 |
| WO | WO02/061880 | 8/2002 |
| WO | WO2004/112628 | 12/2004 |
| WO | WO2005/016119 | 2/2005 |

OTHER PUBLICATIONS

Esterline Product Literature, "Light Key: Visualize a Virtual Keyboard. One With No Moving Parts", Nov. 1, 2003; 4 pages.
H. Schwarzmaier et al.. "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
U.S. Appl. No. 08/483,742, Jun. 7, 1995.
U.S. Appl. No. 08/136,098, Oct. 14, 1993
U.S. Appl. No. 09/195,118, Nov. 18, 1998.
U.S. Appl. No. 10/244,346, Sep. 16, 2002.
U.S. Appl. No. 11/053,987, Feb. 8, 2005.
U.S. Appl. No. 12/023,606, Jan. 31, 2008.
U.S. Appl. No. 12/129,482, May 29, 2008.
U.S. Appl. No. 12/135,425, Jun. 9, 2008.
U.S. Appl. No. 12/135,690, Jun. 9, 2008.
U.S. Appl. No. 12/147,093, Jun. 26, 2008.
U.S. Appl. No. 12/181,504, Jul. 29, 2008.
U.S. Appl. No. 12/184,556, Aug. 1, 2008.
U.S. Appl. No. 12/194,254, Aug. 19, 2008.
U.S. Appl. No. 12/197,601, Aug. 25, 2008.
U.S. Appl. No. 12/197,405, Aug. 25, 2008.
U.S. Appl. No. 12/197,473, Aug. 25, 2008.
U.S. Appl. No. 12/199,935, Aug. 28, 2008.
U.S. Appl. No. 12/203,474, Sep. 3, 2008.
U.S. Appl. No. 12/236,686, Sep. 24, 2008.
U.S. Appl. No. 12/244,850, Oct. 3, 2008.

U.S. Appl. No. 12/250,110, Oct. 13, 2008.
U.S. Appl. No. 12/250,171, Oct. 13, 2008.
U.S. Appl. No. 12/253,457, Oct. 17, 2008.
U.S. Appl. No. 12/277,951, Nov. 25, 2008.
U.S. Appl. No. 12/350,292, Jan. 8, 2009.
U.S. Appl. No. 12/351,633, Jan. 9, 2009.
U.S. Appl. No. 12/353,623, Jan. 14, 2009.
U.S. Appl. No. 12/353,617, Jan. 14, 2009.
U.S. Appl. No. 12/356,650, Jan. 21, 2009.
U.S. Appl. No. 12/366,298, Feb. 5, 2009.
U.S. Appl. No. 12/389,906, Feb. 20, 2009.
U.S. Appl. No. 12/389,915, Feb. 20, 2009.
U.S. Appl. No. 12/395,034, Feb. 27, 2009.
U.S. Appl. No. 12/399,222, Mar. 6, 2009.
U.S. Appl. No. 12/401,268, Mar. 10, 2009.
U.S. Appl. No. 12/413,011, Mar. 27, 2009.
U.S. Appl. No. 12/413,023, Mar. 27, 2009.
U.S. Appl. No. 12/416,583, Apr. 1, 2009.
U.S. Appl. No. 12/419,395, Apr. 7, 2009.
U.S. Appl. No. 12/423,609, Apr. 14, 2009.
U.S. Appl. No. 12/434,903, May 4, 2009.
U.S. Appl. No. 12/436,237, May 6, 2009.
U.S. Appl. No. 12/436,239, May 6, 2009.
U.S. Appl. No. 12/436,231, May 6, 2009.
U.S. Appl. No. 12/472,831, May 27, 2009.
U.S. Appl. No. 12/475,082, May 29, 2009.
U.S. Appl. No. 12/476,960, Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul., 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™ " Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" in William RH, Rengachary SS (eds): Neurosurgery, New York: McGraw-Hill, vol. 111, (1984), pp. 2490-2499.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N. J., 1970.
Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDtech product literature (Mar. 2000) I'D Wire: product description, 1 page.
MDtech product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) Vol, 1, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Oapril 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: a New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
S. Humphries Jr. et al., "Finite•Element Codes to Model Electrical Heating and Non•Linear Thermal Transport in Biological Media", Proc. ASME HTD-355, 131 (1997).
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: a Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.

European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.

* cited by examiner

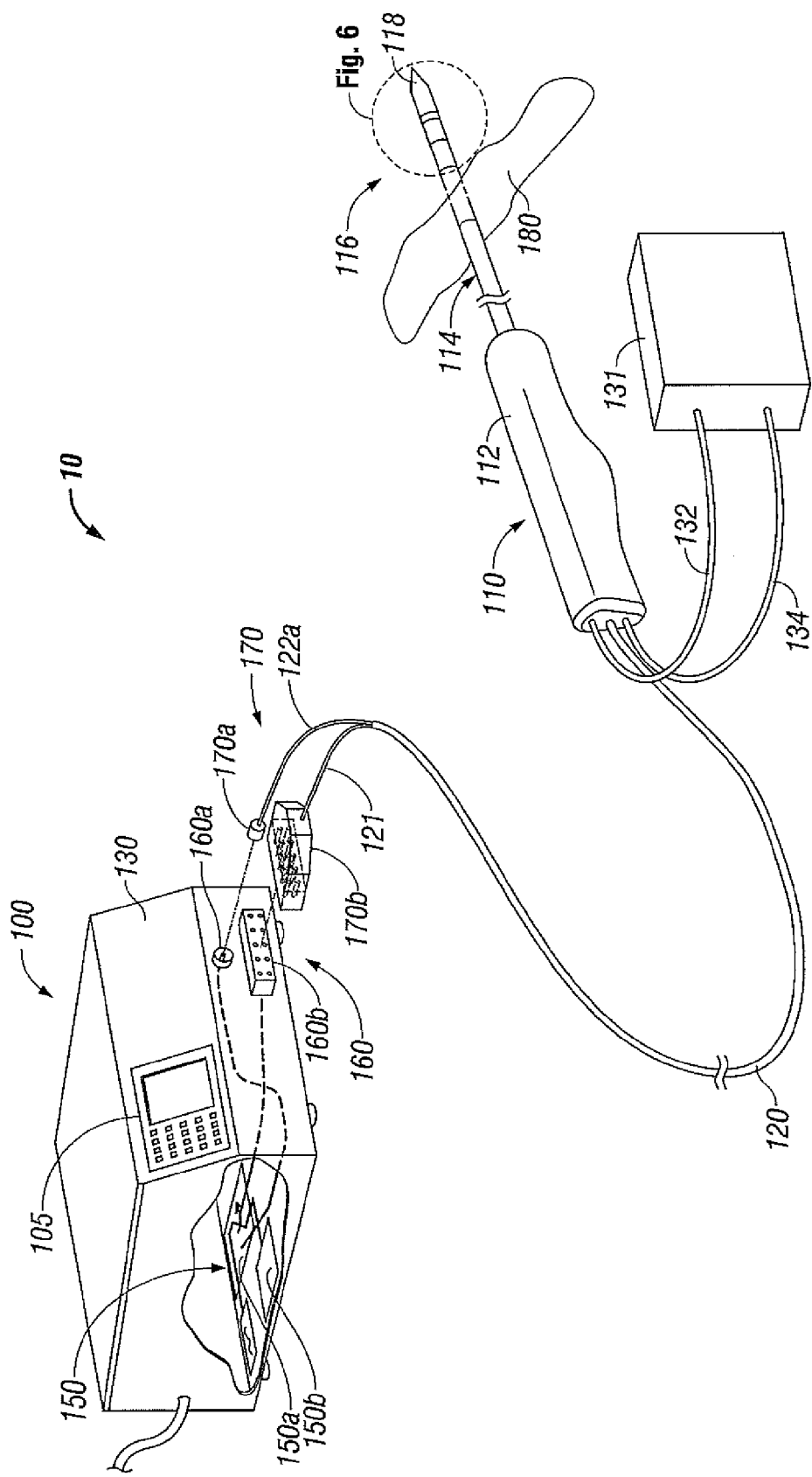

POWER-STAGE ANTENNA INTEGRATED SYSTEM WITH HIGH-STRENGTH SHAFT

BACKGROUND

1. Technical Field

The present disclosure relates generally to microwave systems and devices. More particularly, the present disclosure relates systems and devices for microwave and millimeter-wave signal transmission, amplification and energy delivery to tissue.

2. Background of Related Art

In the treatment of diseases such as cancer, certain types of cancer cells have been found to denature at elevated temperatures (which are slightly lower than temperatures normally injurious to healthy cells). These types of treatments, known generally as hyperthermia therapy, typically utilize electromagnetic radiation to heat diseased cells to temperatures above 41° C. while maintaining adjacent healthy cells at lower temperatures to insure that irreversible cell destruction does not occur. Other procedures utilizing electromagnetic radiation to heat tissue also include ablation and coagulation of the tissue. Such procedures, e.g., such as those performed for menorrhagia, are typically performed to ablate and coagulate the targeted tissue to denature or kill the tissue. Many procedures and types of devices utilizing electromagnetic radiation therapy are known in the art and are typically used in the treatment of tissue and organs such as the prostate, heart, and liver.

Electronic heating of tissue may be accomplished by at least two methods. A first method of electronic heating utilizes the production or induction of an electric current in tissue. An electric current may be produced between two electrodes, between an electrode and a return pad or the current may be induced by an oscillating electric field. As such, heating with an electric current requires the tissue to be conductive or at least partially conductive.

A second method of electronic heating, which utilizes dipolar rotation wherein heat is generated by the movement of molecules by an electric field, is known as dielectric heating. Dielectric heating requires the use of energy in or around a microwave frequency and generates heat in both conductive and nonconductive tissues.

The basic components of the microwave energy delivery system are similar to the components that comprise a conventional microwave ablation system and included a power source and impendence matching circuit to generate microwave energy and an electrode means for delivering the microwave energy to tissue. The microwave generator circuit connects to the electrode by any known suitable connection. Present microwave energy delivery systems include a microwave generator that connects to a microwave energy delivery device, i.e., a tissue penetrating or catheter device, via a semi-rigid coaxial cable.

While many advances have been made in the field of electrosurgical microwave ablation, a conventional electrosurgical microwave system still includes separate components for microwave signal generation, microwave signal transmission and microwave energy delivery (i.e., a generator, coaxial cable and delivery device).

SUMMARY

The present disclosure moves away from the prior art systems that provides individual components performing separate and distinctive functions. The task of microwave signal amplification is distributed between the microwave generator and a power-stage device thereby eliminating the need for the energy transmission device to transmit a high power microwave energy signal.

The present disclosure relates to a microwave antenna assembly for applying microwave energy. The assembly includes a proximal radiating section, a distal radiating section distal the proximal radiating section and a junction member. The proximal radiating includes an inner conductor, an outer conductor, a DC power conductor and a DC neutral conductor, each extending therethrough. The inner conductor is disposed within the outer conductor and the DC power conductor and DC neutral conductor are disposed radially outward from the outer conductor. The junction member mates the distal radiating section and proximal radiating section such that the proximal radiating section and the distal radiating sections are fixedly positioned relative to one another by a mechanically-engaging joint. The junction member further includes a microwave signal amplifier configured to receive a microwave signal at a first energy level from the inner conductor and the outer conductor and configured to receive a DC power signal from the DC power conductor and the DC neutral conductor. The microwave signal amplifier amplifies the microwave signal from the first energy level to an additional level (e.g., a second energy level), the additional energy level being greater than the first energy level. The junction member is further configured to provide the microwave signal at the additional energy level to the proximal radiating section and the distal radiating section.

The proximal radiating section and distal radiating section are adapted to radiate upon transmission of radiation through the antenna assembly. The length of the proximal radiating section and the distal radiating section are proportional to an effective wavelength of the radiation transmitted by the antenna assembly. The distal radiating section may include a metal, a dielectric material or a metamaterial.

The microwave antenna assembly may include a dielectric coating disposed at least partially over the antenna assembly. The junction member electrically insulates the distal radiating section and the proximal radiating section.

In another embodiment, the proximal radiating section has a length corresponding to a distance of one-quarter wavelength of the radiation transmittable through the antenna assembly. The proximal radiating section radiates along the length upon transmission of the radiation.

In yet another embodiment, the junction member further includes a first step and a second step such that the junction member includes at least two different radial thicknesses. The first step receives one of the inner conductor, the outer conductor, the DC power conductor and the DC neutral conductor. The distal radiating section may include a tapered distal end.

BRIEF DESCRIPTION OF THE DRAWINGS

Various embodiments of the present disclosure are described herein with reference to the drawings wherein:

FIG. 1 is a perspective view of an electrosurgical system according to an embodiment of the present disclosure;

DETAILED DESCRIPTION

Figure 2A:
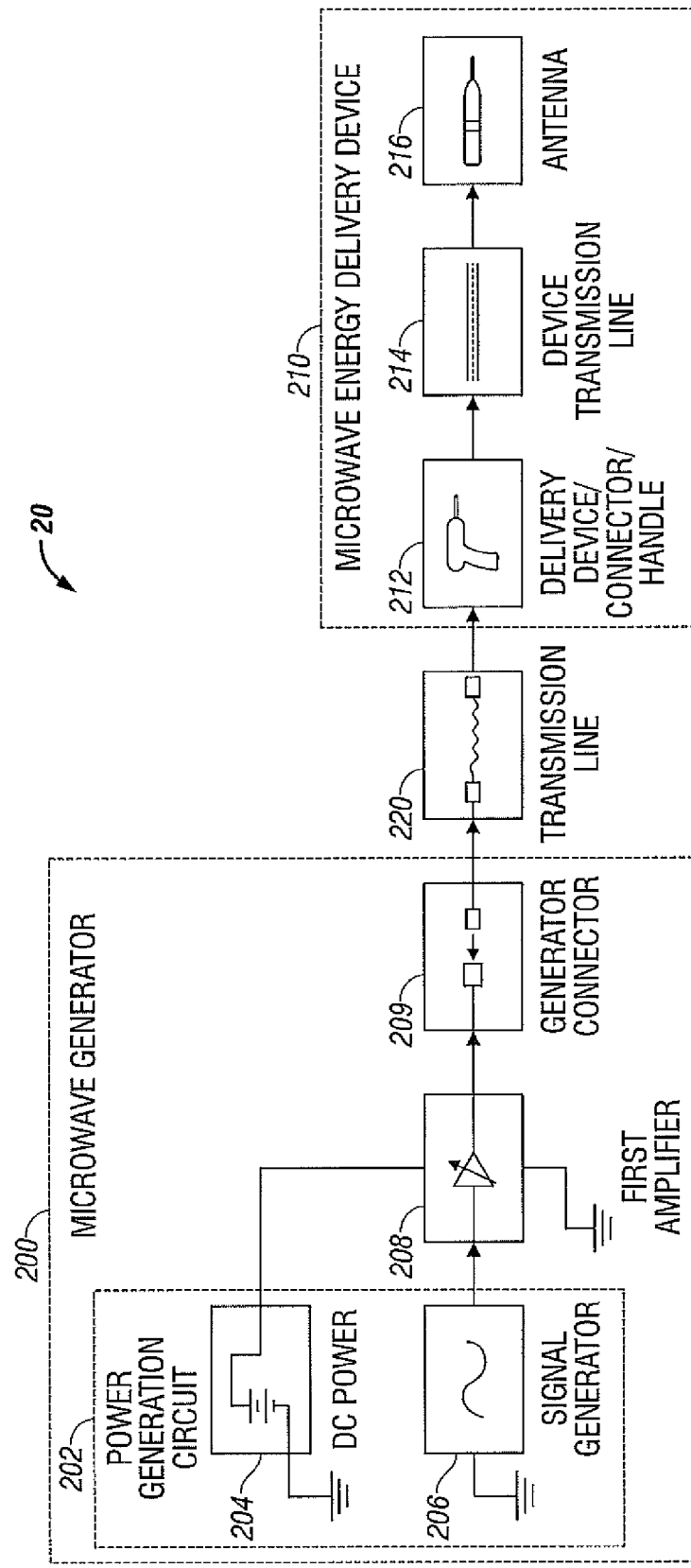
FIG. 2A is a block diagram illustrating the various functional components of a conventional microwave generation and delivery system.

Embodiments of the presently disclosed microwave antenna assembly are described in detail with reference to the drawing figures wherein like reference numerals identify similar or identical elements. As used herein and as is traditional, the term "distal" refers to the portion that is furthest from the user and the term "proximal" refers to the portion that is closest to the user. In addition, terms such as "above", "below", "forward", "rearward", etc. refer to the orientation of the figures or the direction of components and are simply used for convenience of description.

During treatment of diseased areas of tissue in a patient, the insertion and placement of an electrosurgical energy delivery apparatus, such as a microwave antenna assembly, relative to the diseased area of tissue is critical for successful treatment. Generally, the microwave antenna assemblies described herein allow for direct insertion into tissue and include a half-wave dipole antenna at the distal end. An assembly that functions similarly to the may be found in U.S. Pat. No. 6,878,147 to Prakash, issued on Apr. 12, 2005, which is herein incorporated by reference.

While the present disclosure describes specific modifications and changes to that which is described in Prakash, this disclosure should not be construed as being limited to incorporation with the Prakash microwave energy delivery devices. In addition, while the present disclosure is described in the context of microwave energy generation and delivery, the present disclosure may incorporate any suitable electrosurgical frequency. Other suitable applications are contemplated, such as telecommunications, sensing, imaging, sterilizing and cleaning.

Power-Stage Ablation System

Referring now to FIG. 1, a power-stage antenna integrated microwave ablation system (hereinafter "power-stage ablation system"), according to an embodiment of the present disclosure, is shown as system 10. Power-stage ablation system 10 includes a power-stage microwave signal generator 100 (hereinafter "power-stage generator") connected to a power-stage microwave energy delivery device 110 (hereinafter "power-stage device") via a transmission line 120 and, in some embodiments, a cooling fluid supply 131. Power-stage generator 100 includes a housing 130 that houses a power generation circuit 150 that includes a microwave signal circuit 150a and a DC power circuit 150b. A delivery device port 160 defined in generator 100 operably connects to a device connector 170 at one end of the transmission line 120.

Power-stage device 110 includes a handle 112 and an elongate shaft 114 including an antenna 116 on a distal end thereof. Distal portion of antenna 116 may form a sharpened tip 118 for percutaneous insertion into patient tissue 180. If present, a cooling fluid supply 131 may supply cooling fluid to power-stage device 110 via supply and return tubes 132, 134, respectively, connected to the proximal end of handle 112.

Power-stage device 110 may be intended for use with either the power-stage ablation system 10 of the present disclosure and/or in a conventional system that supplies high power microwave energy to a conventional microwave energy delivery device (e.g., a power-stage device may emulate a conventional microwave energy delivery device thereby allowing the power-state device to be utilized in either a conventional system or a power-stage ablation system).

While the present disclosure describes a power-stage ablation system 10 and methods of use with a percutaneous type delivery device, the systems and methods disclosed herewithin may be used with, or incorporated into, any suitable type of electrosurgical energy delivery device capable of delivering electrosurgical energy, such as, for example, an open device, a catheter-type device, an endoscopic device, a surface delivery device and an RF energy delivery device.

Conventional Microwave Ablation System

FIG. 2A is a block diagram illustrating the various functional components of a conventional microwave energy generation and delivery system 20. Conventional system 20 includes a microwave generator 200, a transmission line 220 and a microwave energy delivery device 210. Microwave generator 200 includes a power generation circuit 202 that generates and provides DC power from the DC power supply 204 and a microwave signal from the signal generator 206. DC power and the microwave signal are supplied to a first amplifier 208 that amplifies the microwave signal to a desirable power level.

First amplifier 208 may include one or more power amplifiers or other suitable means to amplify the microwave signal generated by the single generator 206 to a desirable energy level.

The microwave signal from the first amplifier 208 is supplied to a first end of the transmission line 220 connected to the generator connector 209. The second end of the transmission line 220 connects to the delivery device connector 212 of the microwave energy delivery device 210. The microwave signal is passed through the device transmission line 214 to the antenna 216 at the distal end of the microwave energy delivery device 210.

Figure 2B:
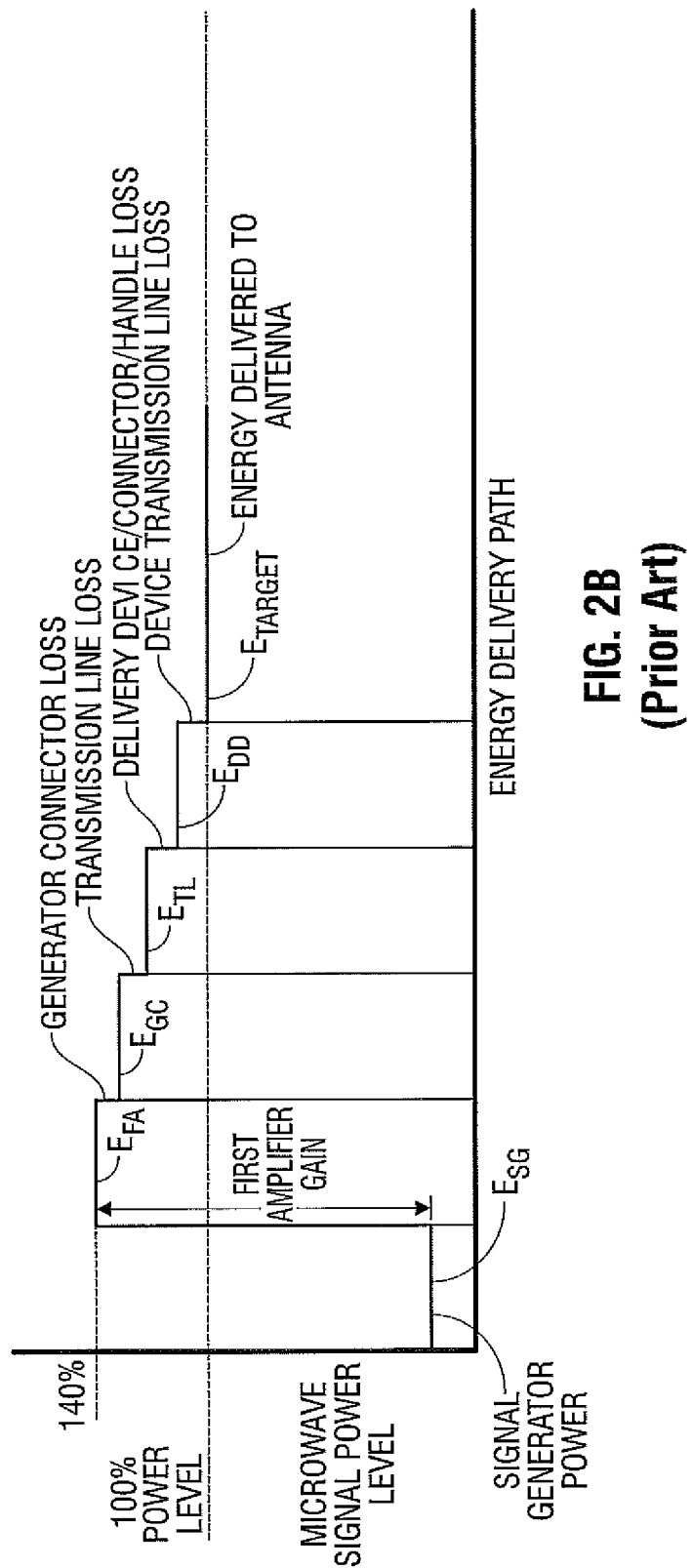
FIG. 2B is a graphical illustration of the microwave signal power level at the various functional components of FIG. 2A.

FIG. 2B is a graphical illustration of the microwave signal power level at the various functional components of the conventional microwave energy generation and delivery system 20 of FIG. 2A. The desirable amount of energy delivered to antenna 216 is illustrated on the graph as 100% Power Level and shown as $E_{TARGET}$. FIG. 2B further illustrates the signal strength of the microwave signal at each component of the conventional system 20 of FIG. 2A.

With continued reference to FIGS. 2A and 2B, microwave signal strength at the signal generator 206 is represented as $E_{SG}$ in the first block of the illustration. The microwave signal is amplified by the first amplifier 208, based on a desirable amplifier gain, to a suitable microwave signal strength $E_{FA}$ as illustrated in the second block. In a conventional system 20, signal amplification is only performed in the microwave generator 200, therefore, the first amplifier 208 must amplify the microwave signal to a suitable microwave power strength to overcome power losses between the first amplifier 208 and the antenna 216 (i.e., $E_{FA}$ is greater than $E_{TARGET}$ to compensate for system losses between the first amplifier 208 and the antenna 216).

Components between the first amplifier 208 and the antenna 216 in a conventional system 20 of FIG. 2A may result in a loss of at least a portion of the microwave signal strength. For example, in FIGS. 2A and 2B signal loss may occur at any one of the generator connector 209, the transmission line 220, the deliver device connector/handle 212 and the device transmission line 214. Types of energy losses may be due to energy reflecting back toward the signal generator 206, the generation of thermal energy in a component or the unintentional transmission of microwave energy (i.e., a component acting as an antenna and discharging microwave energy).

More specifically, the microwave signal strength $E_{FA}$ at the first amplifier 208 is decreased to $E_{GC}$ at the generator connector 209, $E_{TL}$ at the transmission line 220, $E_{DD}$ at the delivery device connector/handle 212 and $E_{TARGET}$ at the antenna 216. In an actual system the signal loss will depend on the number of components and type of components between the first amplifier 208 and the antenna 216. (The system components provided in FIGS. 2A and 2B are provided as an example and do not include all components between the amplifier and the antenna in an actual system.)

In a conventional microwave ablation system losses, as illustrated in FIG. 2B, are from a high power microwave signal $E_{FA}$. As such, the energy losses at each component are a percentage of the high power microwave signal $E_{FA}$. In a conventional system that transmits a high power microwave signal losses can be significant and can potentially be dangerous to the patient and/or the clinician. For example, losses in the transmission line 220 may be due to internal heating, transmission of the microwave signal and/or energy reflected by a connector thereof or the microwave energy delivery device or heating may occur from unintentional energy transmission (i.e., at least a portion of the transmission line acting as an antenna and transmitting energy at the fundamental frequency or a harmonic frequency thereof). Transmission line heating and inadvertent transmission of energy may result in patient or clinician burn and/or energy transmissions that exceed one or more limitations provided in a FCC regulations and/or a standard for electromagnetic compatibility (EMC).

Energy losses in the conventional system 20 are exacerbated because conventional systems 20 operate with a high power microwave signal. For example, a semi-rigid coaxial cable, which is typically very efficient at transferring low power microwave signals, is less efficient when transmitting a high power microwave signal. In addition, when operating at high power levels the transmission line may act as an antenna and radiate microwave energy thereby potentially causing harm to the patient, the clinician or in violation of FCC regulations.

In use, signal generator 206 generates a low power signal, $E_{SG}$, which is supplied to the first amplifier 208. The power delivered to the antenna 216 is equal to 100% on the power level scale and labeled "Target Power Delivery" and shown as $E_{TARGET}$ in FIG. 2B. In order to compensate for energy losses in the system 20 the first amplifier 208 must amplify the microwave signal to a power level of $E_{FA}$, wherein $E_{FA}$ is much greater than the target power delivery, $E_{TARGET}$ (i.e., $E_{FA}$ approximately 140% of $E_{TARGET}$). Losses in the system 20 may include a loss at the generator connector 209, a loss at the transmission line 220, a loss at the delivery device connector and handle 212 and a loss at the device transmission line 214.

As a result thereof, a majority of the energy provided to the antenna 216 is transmitted into tissue and generates heat through dipolar rotation. A portion of the energy delivered to tissue may induce localized currents and finally at least a portion of the energy may result in heating of the antenna portion (heating of the actual antenna, while not ideal, is tolerable since the heat will conduct to the surrounding tissue).

The power-stage ablation system of the present disclosure distributes at least a portion of the power amplification from the microwave generator to another part of the system thereby reducing the energy in the microwave signal transmitted by the transmission line. As such, energy losses of the power-stage ablation system are much lower in magnitude than the energy losses of a conventional microwave ablation system.

Power-Stage Ablation System

Figure 3A:
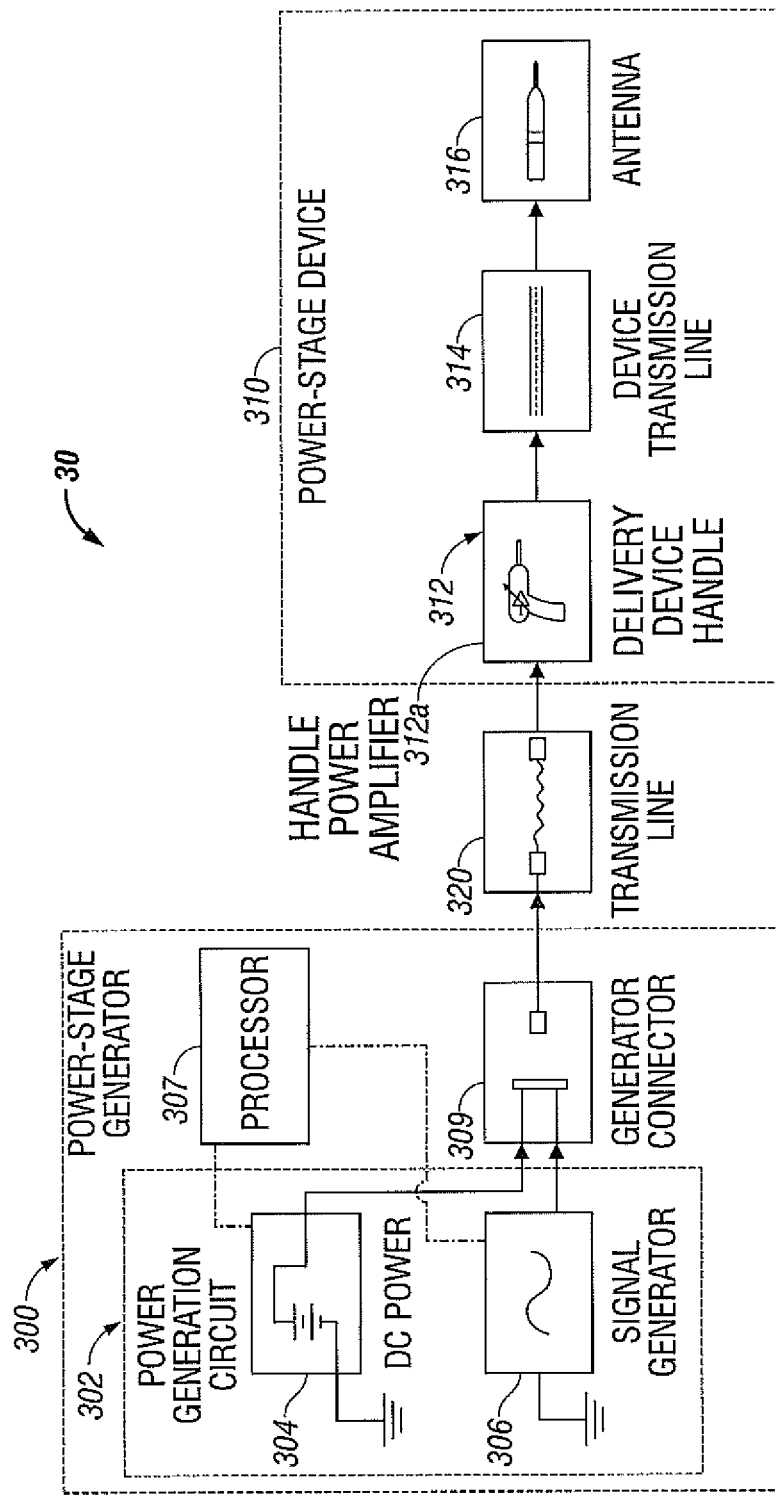
FIG. 3A is a block diagram illustrating the various functional components of a power-stage ablation system according to one embodiment of the present disclosure.

FIG. 3A is a block diagram illustrating the various functional components of one embodiment of the power-stage ablation system of FIG. 1 and is shown as power-stage ablation system 30. Power-stage ablation system 30 includes a power-stage generator 300, a transmission line 320 and a power-stage device 310. Power-stage generator 300 includes at least a power generation circuit 302 that generates DC power from the DC power supply 304 and a microwave signal from the signal generator 306 and a processor 307. DC power and the microwave signal are supplied to the power-stage generator connectors 309. Signal generator 306 may include one or more amplifiers to amplify the signal to a desirable power level. The various other components of a conventional microwave generator known in the art are not discussed in the present disclosure.

Transmission line 320 transfers a DC power signal and a microwave signal from power-stage generator connectors 309 to the handle 312 of the power-stage device 310. Power-stage device 310 includes a delivery device handle 312, a device transmission line 314 and an antenna 316, wherein the delivery device handle 312 includes a handle power amplifier 312a. The handle power amplifier 312a receives a DC power signal and a microwave energy signal from the power generation circuit 302 and amplifies the microwave signal to a desirable or target energy level. Various embodiments of the handle power amplifier 312a are described in detail hereinbelow.

Figure 3B:
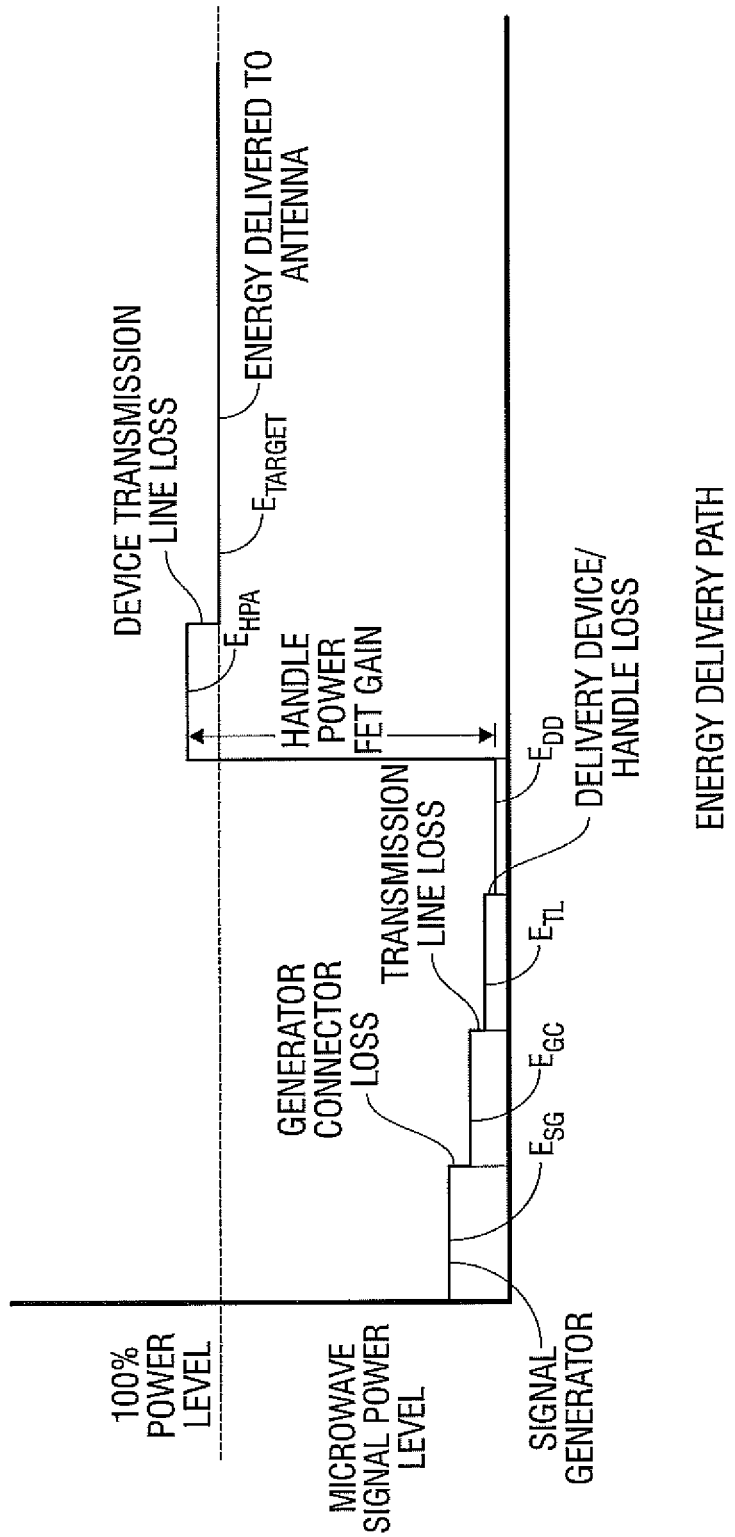
FIG. 3B is a graphical illustration of the microwave signal power level at the various functional components of FIG. 3A.

FIG. 3B is a graphical illustration of the microwave signal strength at the various functional components of the power stage ablation system 30 of FIG. 3A. The desirable amount of energy delivered to antenna 316 is illustrated on the graph as 100% Power Level and shown as $E_{TARGET}$. FIG. 3B further illustrates the signal strength at a component in the power-stage ablation system 30 and the difference between two adjacent bars is equal to the energy losses that occur at each component. The components included in FIGS. 3A and 3B are for illustrative purposes and do not reflect all of the actual components in the system 30.

With continued reference to FIGS. 3A and 3B, signal generator 306 generates a microwave energy signal with an energy level of $E_{SG}$. The microwave signal is supplied to the generator connector 309, along with the DC power signal from the DC power supply 304, and transmitted to the power-stage device 310 through the transmission line 320.

Unlike the conventional microwave ablation system, as described hereinabove and illustrated in FIGS. 2A and 2B, the power-stage ablation system 30 distributes the task of amplifying the microwave signal between various components in the power-stage ablation system 30. Distribution of the power amplification function decreases the energy of the signal transmitted by the transmission line 320 and in other components in the system.

In the power-stage amplification system 30, the energy of the microwave signal provided to the generator connector 309, the transmission line 320 and the delivery device handle, $E_{GC}$, $E_{TL}$ and $E_{DD}$, respectively, are less than the energy at the respective components in the conventional system of FIG. 2A.

The transmission line 320 and delivery device handle 312 pass the microwave signal, with microwave signal strength equal to $E_{DD}$ and the DC power signal to the handle power amplifier 312a. As illustrated in FIG. 3B, the energy level at the handle power amplifier 312a, $E_{DD}$, is significantly less than $E_{TARGET}$. The handle power amplifier 312a amplifies the signal to an energy level greater equal to $E_{HPA}$. $E_{HPA}$ is slightly greater than $E_{TARGET}$, with the difference between $E_{HPA}$ and $E_{TARGET}$ about equal to the energy losses that occur in the device transmission line 314.

In the present embodiment, amplification of the microwave signal is proportioned between the signal generator 306 in the power-stage generator 300 and the handle power amplifier 312a in the handle 312 of the power-stage device 310. The amplification ratio between the signal generator 306 and the handle power amplifier 312a may range between 1:10 wherein a majority of the microwave signal amplification is performed in the handle and 100:0 wherein all amplification is performed in the signal generator (thereby emulating a conventional system).

The present embodiment and the various other embodiments described hereinbelow are examples of systems that distribute the signal amplification function. Signal amplification may be distributed between two or more locations, such as, for example, between at least two of the signal generator, the power-stage device handle and the power-stage device antenna. The specific embodiments should not be considered to be limiting as various other combinations and locations may be used to distribute the signal amplification function and are therefore within the spirit of the present disclosure.

Distributed signal amplification may be performed by one or more power amplifiers e.g. an FET power amplifier. "FET" is used generically to include any suitable power amplification device or circuit configured to amplify a microwave signal. Examples of FETs include a MOSFET (Metal-Oxide-Semiconductor Field-Effect Transistor), a JFET (Junction Field-Effect Transistor), a MESFET (Metal-Semiconductor Field-Effect Transistor), a MODFET (Modulation-Doped Field Effect Transistor), a IGBT (insulated-gate bipolar transistor), a HEMT (high electron mobility transistor formed of AlGaN/GaN) and a GaN HFET (gallium nitride hetero-junction field effect transistors). Various FET's will be illustrated hereinbelow. Signal generator 306, handle power amplifier 312a or other distributed signal amplification may each include one or more suitable FET devices or any combination or equivalent thereof.

Figure 4:
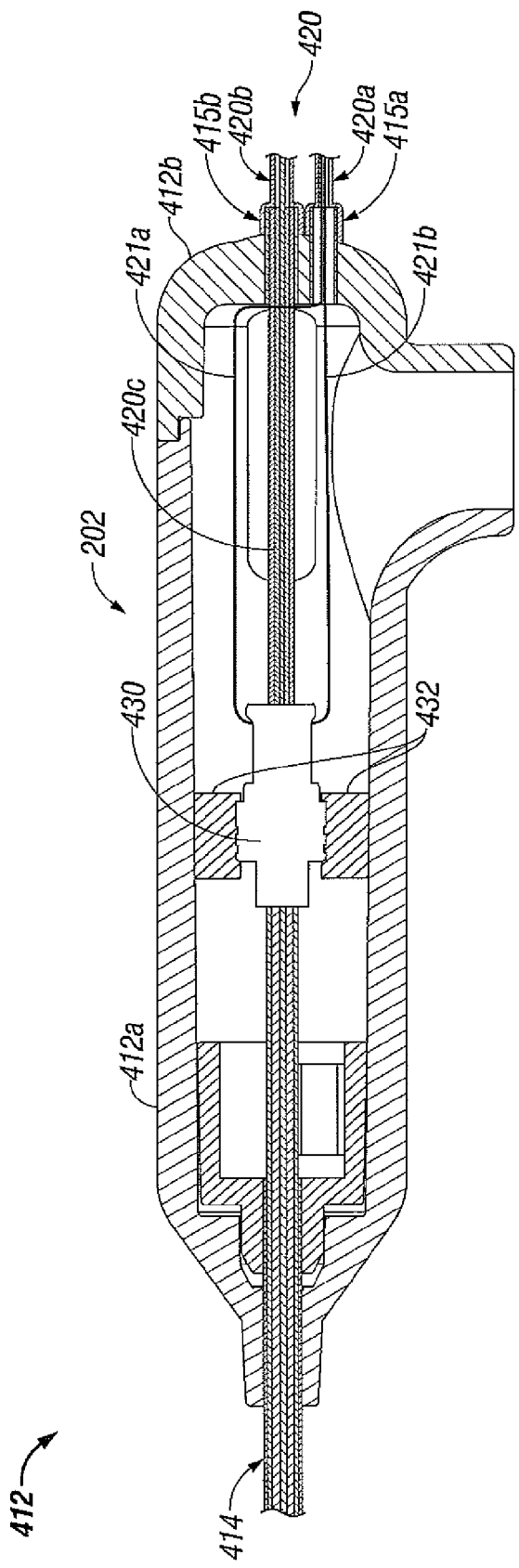
FIG. 4 is an exploded view of the power-stage device of FIG. 1 according to an embodiment of the present disclosure.

FIG. 4 is a cross-sectional view of the handle 412 of the power-stage device 110, 310 of FIGS. 1 and 3A, respectively, according to an embodiment of the present disclosure. Handle 412 receives DC power and a microwave signal from the transmission line 420 through connectors 415a, 415b housed in the proximal portion 412b of handle 412. DC power transmission line 420a provides DC power through the DC connector 415a to the DC positive 421a and DC negative 421b terminals of the handle power amplifier 430. Microwave power transmission line 420b provides a microwave signal to the microwave connector 415b and handle transmission line 420c connects the microwave power transmission line 420b to the handle power amplifier 430.

Handle power amplifier 430 is mounted in the handle 412 and may be supported by one or more amplifier supports 432. Amplifier supports 432 may be formed as part of the handle 412 or may be separate components. Amplifier supports 432 may include active or passive cooling to cool the handle power amplifier 430. In one embodiment, the handle 412 includes active cooling, e.g. the amplifier supports 432 receive cooling fluid from a cooling fluid supply, as illustrated in FIG. 1, and actively cool the handle power amplifier 430. In another embodiment, the handle 412 includes passive cooling, e.g. the amplifier supports 432 are configured to conduct thermal energy away from the handle power amplifier 430. Amplifier supports 432 may be incorporated into handle 412, thereby allowing heat to dissipate through the handle 412 body.

Handle power amplifier 430 amplifies the microwave signal to a desirable energy level, (e.g., to a suitably high power microwave signal level for performing tissue ablation or a desired surgical procedure), and supplies the high power microwave signal to the device transmission line 414 and to the antenna 116 connected to the distal end of the device transmission line 114, as illustrated in FIG. 1.

In some ablation procedures, heating of the device transmission line 414 may be desirable. For example, it may be desirable to ablate at least a portion of the insertion track created in the patient tissue by the sharpened tip when the power-stage device is percutaneously inserted into the patient tissue. In one embodiment, the device transmission line 414 is configured as a heat sink for the handle power amplifier 430 and may dissipate at least some thermal energy generated by the handle power amplifier 430 to tissue.

With reference to FIG. 3A, power stage generator 300 may be configured to control the microwave signal amplification distribution between the signal generator and additional amplifier in the power-stage amplification system 30. Processor 307 of the power-stage generator 300 may control the amplification of one or more of the amplifiers in the power-stage amplification system 30. For example, amplification of the microwave signal by the signal generator 306 may be fixed to provide a microwave signal to the transmission line at a fixed energy level. The microwave signal may be variably amplified to a target energy level by a second amplifier as also described herein. In another embodiment, the gain of the signal generator and the gain of the second amplifier, as described herein, are selectively controlled such that the combined gain of the amplifiers amplifies the microwave signal to a target energy level. The ratio of the gain between the two amplifiers may range from 100% of the gain at the signal generator (wherein the power-stage amplification system emulates a conventional system) and 10% gain at the signal generator and 90% of the gain at the second amplifier, as described herein.

The gain of the second amplifier, as described herein, may be controlled by varying the voltage of the DC power signal. Control may be open-loop wherein the processor 307 of the power-stage generator 300 estimates the voltage of the DC power signal required to generate the gain required from the second amplifier to amplify the microwave signal to the target energy level. In another embodiment, the power-stage amplification system may include closed-loop control wherein the output of the second amplifier or a measurement of the microwave signal provided to antenna is provided to the processor 307 as feedback to the closed-loop control system. The measurement of the microwave signal may be any suitable microwave signal measurement such as, for example, forward and/or reflected power from a dual directional coupler.

Amplifier gain may be selectively controlled by the processor or the clinician. The second amplifier, as described herein, may not provide signal amplification if selected output to the antenna is below an output threshold. For example, at a low power output the signal generator 306 may provide about 100% of the required amplification (i.e., operating similar to a conventional system). As the power output is selectively increased, the microwave signal amplification may be distributed between the signal generator 306 and the second amplifier in the power-stage device. The power output may be selectively increased by a manual input to the power-stage generator 300 by a clinician or may be selectively increased and/or actively changed by an output algorithm performed by the processor 307.

Figure 5A:
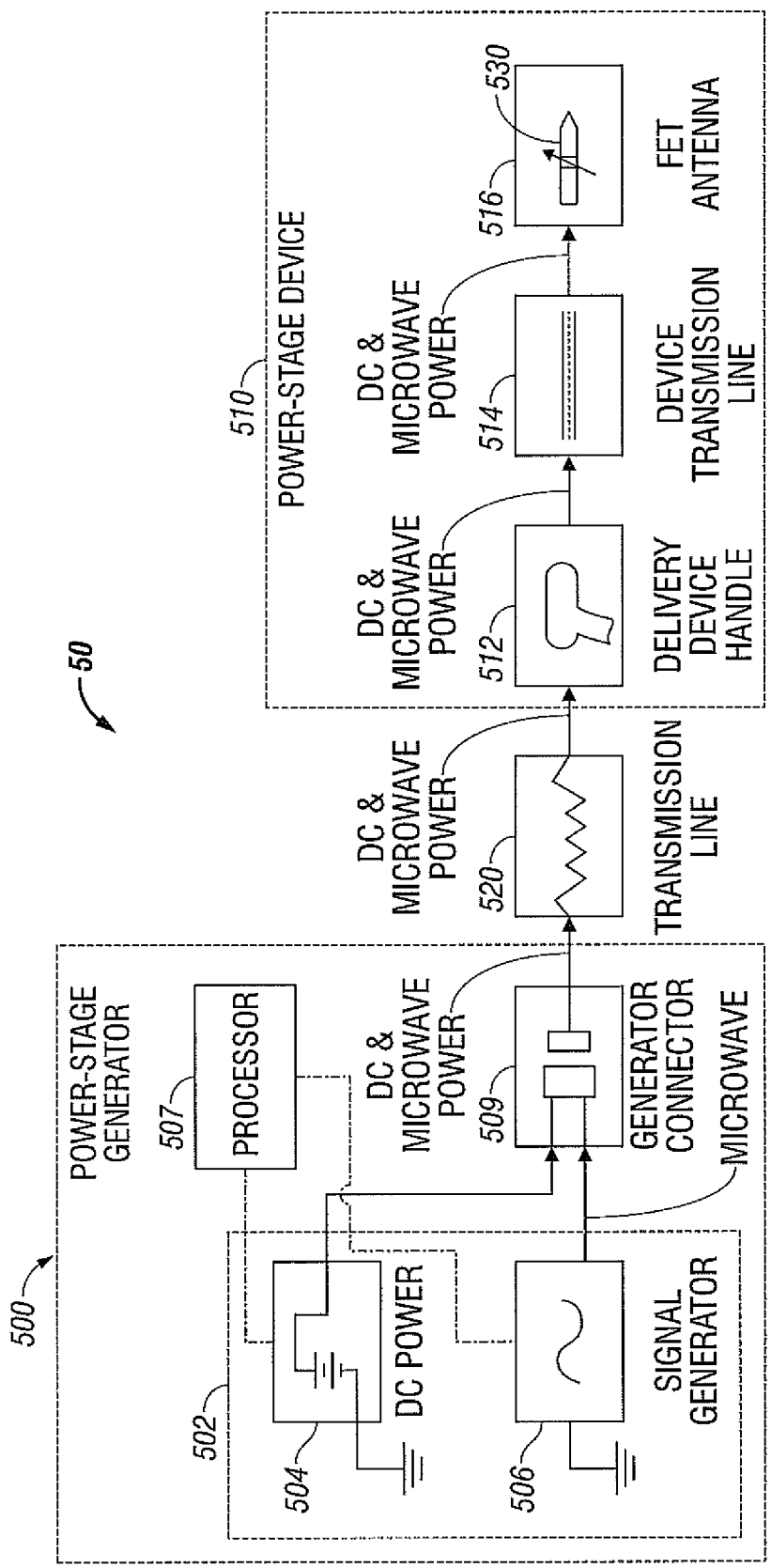
FIG. 5A is a block diagram illustration the various functional components of a microwave generation and delivery system according to another embodiment of the present disclosure.

FIG. 5A is a block diagram illustrating the various functional components of another embodiment of the power-stage ablation system of FIG. 1 and is shown as 50. Power-stage ablation system 50 includes a power-stage generator 500, a transmission line 520 and a power-stage device 510. Power-stage generator 500 includes a power generation circuit 502 that generates DC power from the DC power supply 504 and a microwave signal from the signal generator 506 and a processor 507. DC power and the microwave signal are supplied to the power-stage generator connectors 509. Signal generator 506 may include one or more amplifiers to amplify the microwave signal to a desirable power level.

Transmission line 520 transfers a DC power signal and a microwave signal from power-stage generator connectors 509 to the handle 512 of the power-stage device 510. Power-stage device 510 includes a delivery device handle 512, a device transmission line 514 and an power-stage antenna 516, wherein the power-stage antenna 516 includes an antenna power amplifier 530 configured to amplify the microwave signal generated by the signal generator 506 to a desirable power level. The antenna power amplifier 530 receives a DC power signal and a microwave energy signal from the power-stage generator circuit 502 and amplifies the microwave signal to a desirable or target energy level. Various embodiments of the antenna power amplifier 530 are described in detail hereinbelow.

Figure 5B:
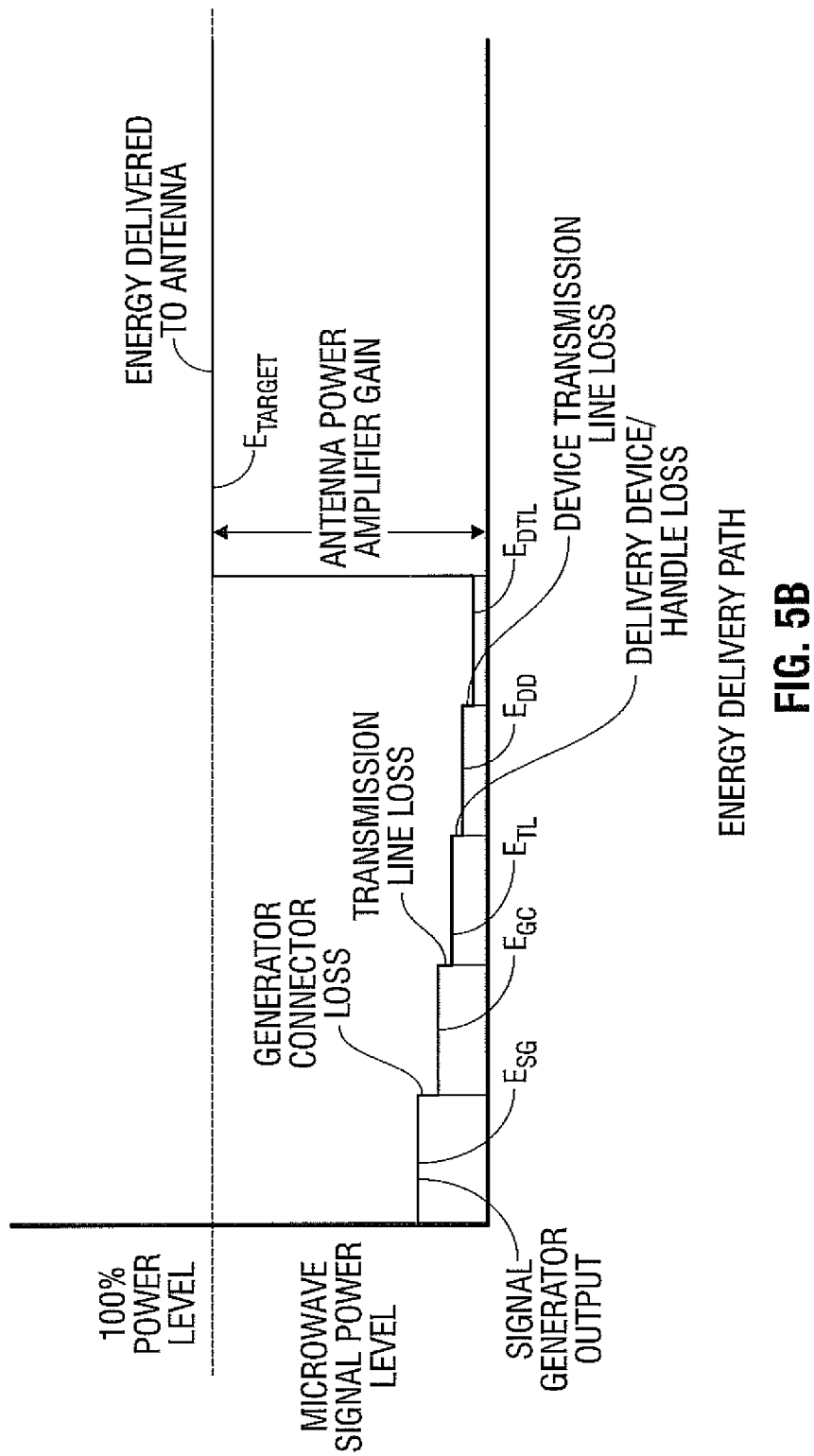
FIG. 5B is a graphical illustration of the microwave signal power level at the various functional components of FIG. 5A.

FIG. 5B is a graphical illustration of the microwave signal power level at the various functional components of FIG. 5A. The targeted energy delivered to antenna 516 is illustrated on the graph as 100% power level and shown as $E_{TARGET}$. Each bar illustrates the energy level at a component in the power-stage ablation system 50 and the difference between two adjacent bars is equal to the energy loss at each components. The components included in FIGS. 5A and 5B are for illustrative purposes and do not reflect all components that may be included in a functional power-stage ablation system 10 as illustrated in FIG. 1.

With continued reference to FIGS. 5A and 5B, signal generator 506 generates a microwave signal with an energy level of $E_{SG}$. The microwave signal is supplied to the generator connector 509, along with the DC power signal from the DC power supply 504, and the microwave signal and the DC power signal are transmitted to the power-stage device 510 through the transmission line 520.

Losses between the signal generator 506 and the generator connectors 509 reduce the microwave signal power level from $E_{SG}$ to $E_{GC}$ as illustrated in FIG. 5B. Losses in the transmission line further reduce the microwave signal power level to $E_{TL}$ and losses in the delivery device handle and device transmission line further reduce the microwave signal power level to $E_{DD}$ and $E_{DTL}$, respectively. The microwave signal delivered to the antenna 516 by the device transmission line 514 is amplified by antenna power amplifier 516 to a desirable or target microwave signal power level of $E_{TARGET}$.

A significant difference between the transmission of the microwave signal in a conventional system and the transmission of the microwave signal in the present embodiment of the power-stage ablation system 50 is the energy level of the microwave signal in the transmission path. In the conventional system 20 the energy level of the microwave signal in the transmission path is greater than the target power level to compensate for losses in the transmission path, as illustrated in FIGS. 2A and 2B. In the power-stage ablation system 50 the energy level of the microwave signal in the transmission path is a fraction of the target power level as illustrated in FIGS. 5A and 5B. As such, the energy losses in the transmission path of the power-stage ablation system 50 are much less than the energy losses in the transmission path of the conventional system. The reduction in the microwave signal energy level in the transmission path also decreases the likelihood of unintentional microwave energy discharged therefrom.

In the present embodiment, amplification of the microwave signal is distributed between the signal generator 506 in the power-stage generator 500 and by the antenna power amplifier 530 in the antenna 516 of the power-stage device 510. Signal generator 506 generates a microwave signal with an energy level of $E_{GS}$. The microwave signal power level from the signal generator 506, $E_{SG}$, has sufficient energy to overcome losses in the transmission path between the signal generator 506 and the antenna power amplifier 530. Antenna power amplifier 530 receives the microwave signal with a microwave signal power level of $E_{DTL}$ and amplifies the microwave signal to a microwave signal power level of $E_{TARGET}$. Antenna power amplifier 530 may require and/or include one or more amplification stages and may include one or more FETs.

The transmission line 520 is configured to pass a low power microwave signal and a DC power signal. Transmission line 520 may be configured as a multi-conductor cable that provides both the microwave signal and DC power to the power-stage device 512. For example, a first conductor may be configured as a standard coaxial cable and a second conductor may be configured as a suitable DC power transmission conductor. The DC power transmission conductor may "piggyback" the coaxial cable as is known in the art. Alternatively, device transmission line 514 may include two or more transmission lines to transmit a low power microwave signal and a DC power signal.

Figure 6:
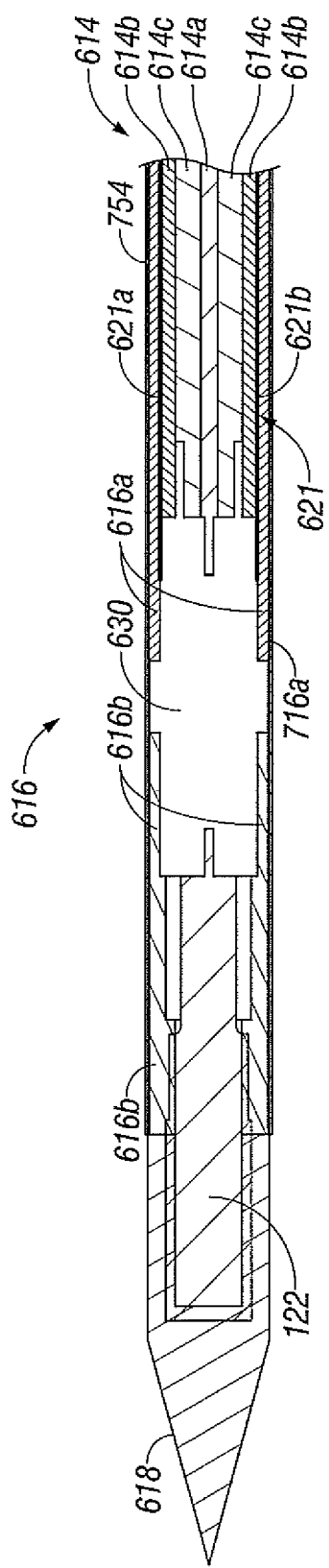
FIG. 6 is a cross-sectional view of the detail area of the antenna portion of the power-stage device of FIG. 1.

As illustrated in FIG. 6, device transmission line 614 is configured to transmit the low power microwave signal and the DC power signal to the antenna power amplifier 630. Device transmission line 614 includes a coaxial arrangement with an inner conductor 614a and an outer conductor 614b separated by a suitable dielectric 614c. A DC power signal may be transmitted through a DC power layer 621 positioned radially outward from the outer conductor 614b. For example, DC power layer may include at least one DC positive trace 621a and at least one DC negative trace 621b insulated from, and printed on, the radial outer surface of the outer conductor 614b. In another embodiment, the DC power signal is transmitted through a suitable conductor pair positioned radially outward from the outer conductor 614b.

The antenna power amplifier may be positioned adjacent the antenna. In one embodiment, the antenna power amplifier is positioned between the distal end of the device transmission line and the proximal end of the antenna. In another embodiment, the antenna power amplifier may be positioned between the distal and proximal radiating sections of the antenna. Antenna power amplifier may include a cylindrical FET described hereinbelow capable of providing sufficient signal amplification of a microwave signal for use in microwave ablation.

FIG. 6 is a cross-sectional view of the antenna 516 of the power-stage device 510 of FIG. 5A and the antenna 116 of FIG. 1 according to one embodiment of the present disclosure. Antenna 616 includes a proximal radiating section 616a, a distal radiating section 616b and an antenna power amplifier 630 positioned therebetween. A sharpened tip 618, distal the distal radiating section 616b, is configured to facilitate percutaneous insertion into tissue. The antenna power amplifier 630 may be a junction member that joins the proximal radiating section 616a and the distal radiating section 616b. The device transmission line 614 connects to at least a portion of the antenna 616 and provides DC power and a microwave signal to the antenna power amplifier 630.

The antenna power amplifier 630 connects the distal radiating section 616b and the sharpened tip 618 to the proximal portion of the antenna and/or the transmission line 614 and may provide support and rigidity to the antenna 616. Antenna power amplifier 630 may connect with a mechanically-engaging joint such as, for example, a press-fit joint, an interface-fit joint, a threaded interface, a pinned joint and an overlap joint. Antenna power amplifier 630 may be adapted to be in a pre-stressed condition to further provide mechanical strength to the antenna.

Antenna power amplifier 630 receives DC power from the DC positive 621a and the DC negative 621b of the device transmission line 614, and microwave power from the inner and outer conductors 614a, 614b, respectively. In this embodiment, the inner portion of the device transmission line 614 is configured as a coaxial waveguide surrounded by two or more conductors 621 that provide the DC power. The two or more conductors 621 may be configured as a twisted pair, a plurality of twisted pair combinations, or any other suitable combination.

DC power may be provided between a plurality of conductors or conductor pairs to distribute the current required by the antenna power amplifier 630. For example, the coaxial waveguide of the device transmission line 614 may be at least partially surrounded by four two-wire twisted pair conductors each supplying about one fourth of the DC power to the antenna power amplifier 630. The arrangement of the conductors around the coaxial waveguide may be configured to minimize noise or to prevent induction of a microwave signal on the conductors.

In a conventional microwave energy delivery system, as discussed hereinabove, the device transmission line transmits a high power microwave signal and any heat generated therein is from the high power microwave signal In the present embodiment, the device transmission line 614 transmits a low power microwave signal and a DC Power signal to the antenna power amplifier 630 where the microwave signal is amplified to a desirable power level. Some thermal energy may still be generated in the device transmission line 614 from both the low power microwave signal and/or the DC power signal. A fluid cooling system, as illustrated in FIG. 1, may be configured to provide cooling fluid to any portion of the device transmission line 614.

In another embodiment, a DC power signal may generate a majority of the thermal energy in the device transmission line 614. As such, the cooling system may be configured to provide cooling to the conductors providing the DC power signal.

Device transmission line 614 may include a fluid cooling system to absorb thermal energy. With reference to FIG. 1, cooling fluid from the cooling fluid supply 131 may circulate through at least a portion of the device transmission line 114. Cooling fluid may absorb thermal energy from the device transmission line (e.g., the conductors that provide the DC power, the coaxial waveguide or both). Cooling fluid may be used to separate the microwave energy waveguide (i.e., the coaxial) and the conductors providing the DC power thereby providing an electromagnetic shield between at least a portion of the coaxial waveguide transmitting microwave energy and the conductors providing DC Power.

As illustrated in FIG. 6, proximal and distal radiating sections 616a, 616b connect to antenna power amplifier 630. Antenna power amplifier 630 receives a microwave signal at a first power level from the inner and outer conductor and a DC power signal from the DC power and DC neutral and amplifies the microwave signal to a second power level. The microwave signal at the second power level is supplied to the radiating sections 616a, 616b. Antenna power amplifier 630 may generate thermal energy during signal amplification. Thermal energy may be absorbed by, or provided to, the surrounding tissue and may contribute to the desired clinical effect.

Figure 7:
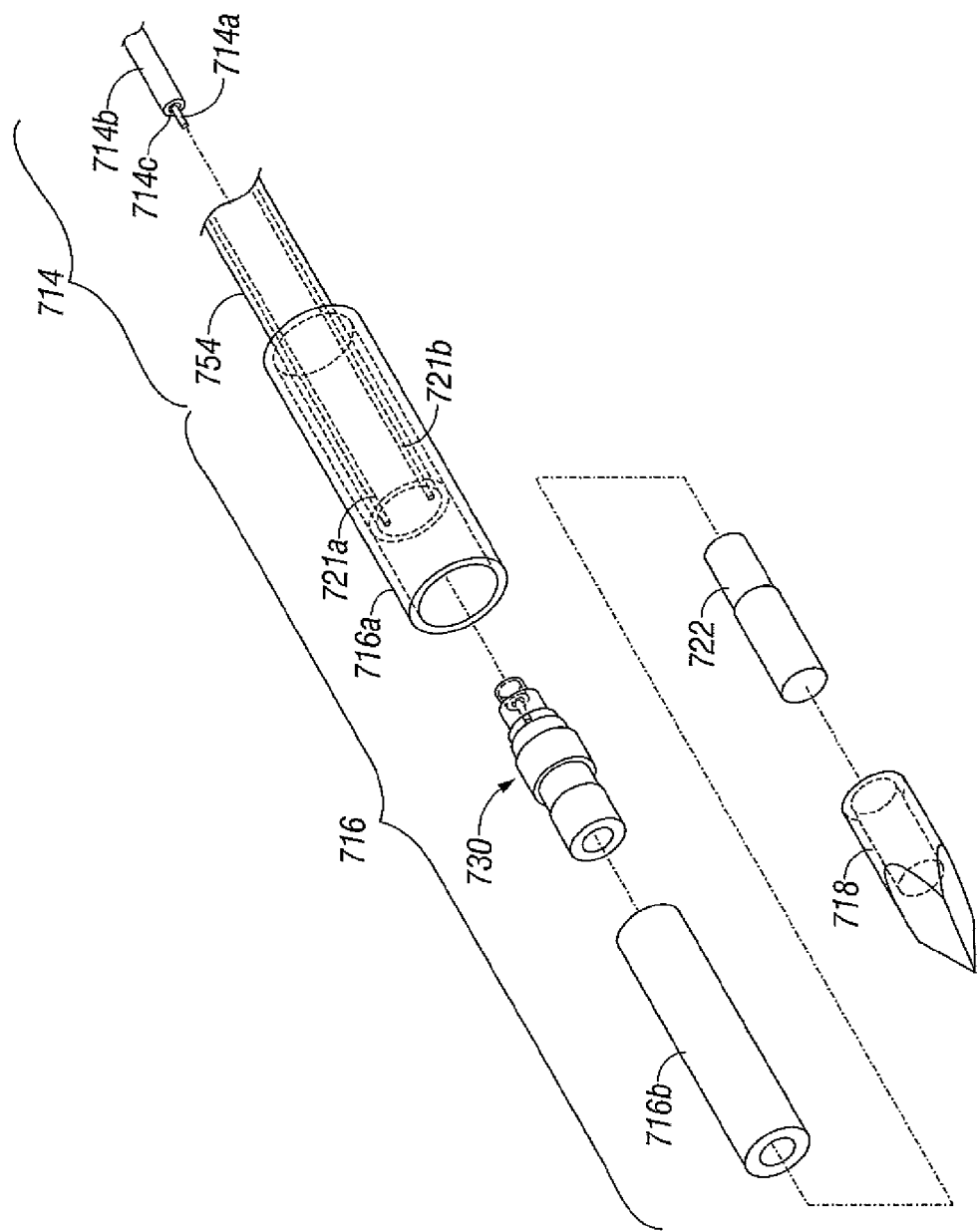
FIG. 7 is an exploded view of the antenna portion of the power-stage device of FIG. 1.

FIG. 7 is an exploded view of the antenna 116 portion of the power-stage device 110 of FIG. 1. The device transmission line 714 connects to the proximal portion of the proximal radiating section 716a and supplies a DC power signal and a microwave signal to the antenna portion 716. The microwave signal is provided through a coaxial waveguide that includes an inner conductor 714a and an outer conductor 714b separated by a dielectric 714c. The DC power signal is provided through at least a pair of DC conductors 721a, 721b that includes a DC positive 721a and a DC negative 721b. DC conductors 721a and 721b may be formed on the inner surface of the insulating coating 754.

The antenna 716 includes a proximal radiating section 716a and a distal radiating section 716b separated by an antenna power amplifier 730. Antenna power amplifier 730 receives the microwave signal and DC power from the device transmission line 714, amplifies the microwave signal to a desirable energy level and provides the amplified microwave signal to the proximal radiating section 716a and the distal radiating section 716b of the antenna 716. A sharpened tip 718 connects to the distal portion of the distal radiating section 716b and is configured to penetrate tissue.

The proximal end the antenna power amplifier 730 connects to the inner conductor 714a, the outer conductor 714b, the DC positive 721a, the DC negative 721b, and the proximal radiating section 716a. The center portion of the antenna power amplifier 730 receives the distal end of the inner conductor 714a and the outer conductor 714b is received radially outward from the center of the antenna power amplifier 730. The antenna power amplifier 730 receives the microwave signal between the inner and outer conductor of the coaxial waveguide. Radially outward from the surface of the antenna power amplifier 730 that receives the outer conductor 714b, the surface of the antenna power amplifier 730 connects to the DC conductors 721a and 721b and receives the DC power signal therefrom. The proximal radiating section 716a of the antenna 716 at least partially surrounds the antenna power amplifier 730 and receives the amplified microwave signal therefrom. Proximal radiating section 716a may also conduct thermal energy away from the antenna power amplifier 730.

The distal end of the antenna power amplifier 730 connects to the proximal end of the distal radiating section 716b and receives the amplified microwave signal therefrom. Distal radiating section 716b may also conduct thermal energy away from the antenna power amplifier 730. Distal radiating section 716b and proximal radiating section 716a together form the two poles of a dipole microwave antenna. In this particular embodiment, antenna 716 is a conventional half-wave dipole microwave antenna and includes a proximal radiating section 716a and a distal radiating section 216b. The antenna power amplifier described herein may be used with any suitable microwave antenna, such as an electrosurgical antenna configured to radiate microwave energy to tissue in an electrosurgical procedure.

Tip connector 722 connects the sharpened tip 718 to the distal end of the distal radiating section 716b. Sharpened tip 718 may be part of the distal radiating section 716b or sharpened tip 718 may connect to distal radiating section 716b and configured to not radiate energy. For example, tip connector 722 may electrically connect or electrically insulate sharpened tip 718 and distal radiating section 716b. In another embodiment, sharpened tip 718 may include a suitable attachment means thereby eliminating the tip connector 722.

In yet another embodiment, the antenna power amplifier 730 is positioned proximal to the proximal radiating section and the proximal and distal radiating sections are separated by a conventional spacer as known in the art.

Figure 8A:
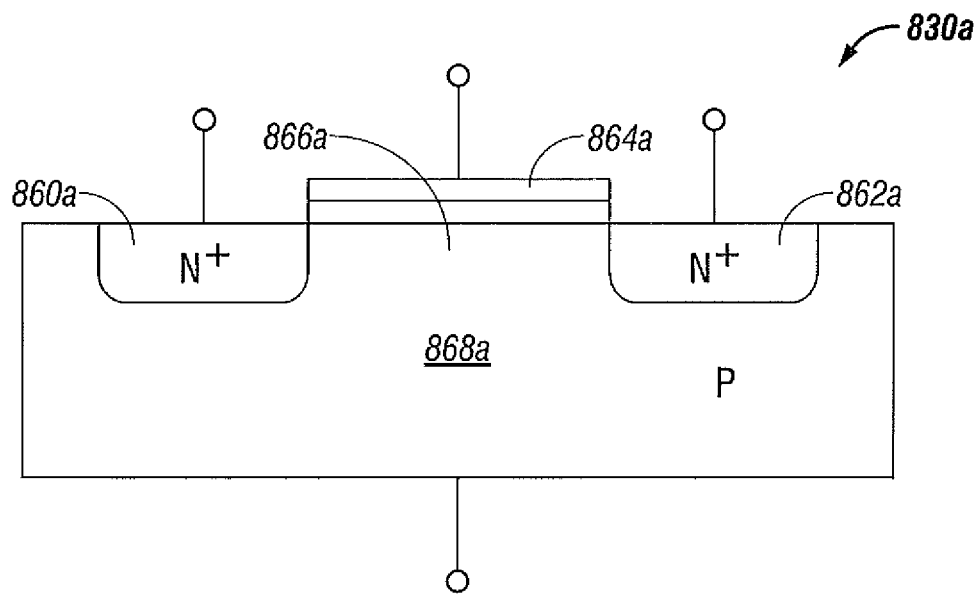
FIG. 8A is a cross section of a typical planar n-type FET.

FIG. 8A is a cross section of a typical n-type FET 830a. The typical FET used for microwave applications use a planar topology in which an active epitaxial layer is placed on a semi-insulating substrate. For example, semi-insulating substrate may include gallium arsenide (GaAs), silicon, germanium or any other suitable material commonly used in semiconductor devices. FET may also include gallium nitride (GaN). GaN may be particularly suited when working with higher temperatures, higher voltages and/or higher frequencies, while producing less heat. On this substrate a conductive layer is deposited and photo-etched to leave structures referred to as a source, gate and drain. Gate terminal 864a controls the opening and closing of the transistor by permitting or blocking the flow of electrons between the source 860a and drain 862a. The gate terminal 862a creates or eliminates a channel in the active layer 866a between the source 860a and the drain 862a and the density of the electron flow is determined by the applied voltage. The body 868a includes the bulk of the semiconductor in which the gate 864a, source 860a and drain 862a lie. With reference to FIG. 7, the antenna power amplifier 730 may be configured to house an n-type FET 830a illustrated in FIG. 8A.

Figure 8B:
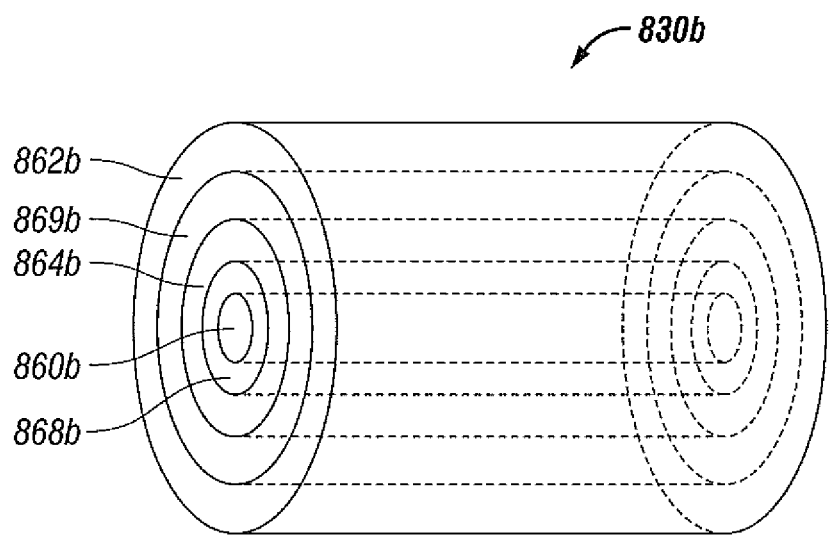
FIG. 8B is an illustration of a cylindrical FET according to one embodiment of the present disclosure.
Figure 8C:
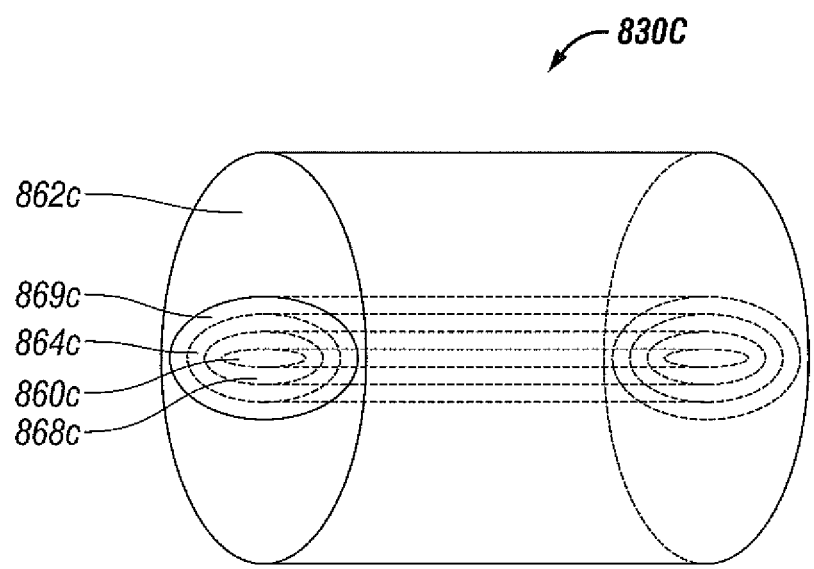
FIG. 8C is an illustration of a cylindrical FET according to yet another embodiment of the present disclosure.

In yet another embodiment of the present disclosure, the antenna power amplifier 730 illustrated in FIG. 7 is formed from a cylindrical FET 830b as illustrated in FIGS. 8B and 8C. In FIGS. 8B and 8C each of the cylindrical FETs 830b, 830c are configured in a cylindrical arrangement to facilitate placement of the cylindrical FETs 830b, 830c in the antenna 116, 716 of the power-stage device 110 antenna 116, 716 of FIGS. 1 and 7, respectively. Starting at the radial center of the cylindrical FET 830b and working radially outward, the layers include a source 860b, 860c, an first epitaxial layer 868b, 868c the gate 864b, 864c, a second epitaxial layer 869b, 869c, and a drain 862b, 862c. The source 860b, 860c may be formed from a center pin, tube or elongate conductive structure on which a first epitaxial layer 868b, 868c is deposited. As illustrated in FIG. 8C, the shape of the center structure need not be circular. Varying the overall shape and structure of the center structure varies the surface area between the source 860b, 860c and the first epitaxial layer 868b, 868c. On the first epitaxial layer 868b, 868c a metal layer is deposited that serves as a gate 864b, 864c. The gate 864b, 864c may have through holes filled with a second epitaxial layer 869b, 869c in order to provide a current "pinch off" effect similar to that used in a planar FET. Alternatively, the gate 864b, 864c may be partitioned into several continuous stripes or strips thereby allowing a control voltage at varying potentials to be applied and to "pinch off" the flow of electrons and control the power output of the cylindrical FET. Many other configurations are possible to allow gate control of the cylindrical FET and are likely to be dictated by geometry and/or the choice of materials. In one embodiment, the metal forming gate 864b, 864c may be gold. Deposited on the second epitaxial layer 869b, 869c is a second conductive layer that serves as drain 862b, 862c. In one embodiment, the drain 862b, 862c acts as the external surface, i.e., a radiating section of the antenna. The drain 864b, 864c is concentrically deposited outside the gate 862b, 862c and second epitaxial layer 869b, 869c sandwich layers.

In use, the DC voltage applied across the source and drain determines the gain of the output stage. The microwave frequency signal is applied to the gate. As such, the gain of the power-stage device is controlled by the signals provided from the power-stage microwave generator.

The cylindrical FET 830b, 830c, while configured to operate similarly to a traditional FET illustrated in FIG. 8A and described hereinabove, is particularly suited for use in microwave ablation devices described herein and used in the art.

In yet another embodiment, the cylindrical FET 830b, 830c may incorporate the use of metamaterial in the FET's construction, the construction of the antenna power amplifier and/or the construction of the distal or proximal radiating section. A metamaterial is an engineered material with a particular structure that provides control of the permittivity and permeability of the material. With metamaterials, the structure, rather than the composition, determines the property of the material. The cylindrical FET may include at least one layer formed of a metamaterial. For example, the drain 862b, 862c may be coated with a metamaterial surface (not shown) or may be formed from a metamaterial such that the metamaterial serves as a electromagnetic wave steerer or refractor, modulator, filter, magnifier or coupler. In one embodiment, the metamaterial produces a non-uniform electromagnetic field around the antenna.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A microwave antenna assembly for applying microwave energy therapy comprising:
   a proximal radiating section having an inner conductor, an outer conductor, a DC power conductor and a DC neutral conductor, each extending therethrough, the inner conductor disposed within the outer conductor and the DC power conductor and DC neutral conductor disposed radially outward from the outer conductor;
   a distal radiating section distal the proximal radiating section; and
   a junction member configured to mate the distal radiating section and proximal radiating section such that the proximal radiating section and the distal radiating sections are fixedly positioned relative to one another by a mechanically-engaging joint, the junction member further configured to include:
      a microwave signal amplifier configured to receive a microwave signal at a first energy level from the inner conductor and the outer conductor and configured to receive a DC power signal from the DC power conductor and the DC neutral conductor, the microwave signal amplifier further configured to amplify the microwave signal from the first energy level to at least one second energy level, the at least one second energy level being greater than the first energy level,
wherein the junction member is further configured to provide the microwave signal at the second energy level to the proximal radiating section and the distal radiating section.

2. The microwave antenna assembly of claim 1 wherein the proximal radiating section and distal radiating section are adapted to radiate upon transmission of radiation through the antenna assembly.

3. The microwave antenna assembly of claim 2 wherein the proximal radiating section and the distal radiating section have a length which is proportional to an effective wavelength of the radiation transmitted by the antenna assembly.

4. The microwave antenna assembly of claim 1 wherein the distal radiating section comprises at least one of a metal, a dielectric material and a metamaterial.

5. The microwave antenna assembly of claim 1 further comprising a dielectric coating disposed at least partially over the antenna assembly.

6. The microwave antenna assembly of claim 1, wherein the junction member electrically insulates the distal radiating section and the proximal radiating section.

7. The microwave antenna assembly of claim 1 wherein the proximal radiating section has a length corresponding to a distance of one-quarter wavelength of radiation transmittable through the antenna assembly.

8. The microwave antenna assembly of claim 7 wherein the proximal radiating section is adapted to radiate along the length upon transmission of the radiation.

9. The microwave antenna assembly of claim 1 wherein the junction member further includes a first step and a second step such that the junction member comprises at least two different radial thicknesses,
wherein the first step is configured to receive at least one of the inner conductor, the outer conductor, the DC power conductor and the DC neutral conductor.

10. The microwave antenna assembly of claim 1 wherein the distal radiating section has a tapered distal end.

* * * * *

UNITED STATES PATENT AND TRADEMARK OFFICE
CERTIFICATE OF CORRECTION

PATENT NO. : 8,463,396 B2  
APPLICATION NO. : 12/436239  
DATED : June 11, 2013  
INVENTOR(S) : Ronald J. Podhajsky Page 1 of 1

It is certified that error appears in the above-identified patent and that said Letters Patent is hereby corrected as shown below:

On the title page item (73), Assignee "LLP" should be changed to --LP--.

Signed and Sealed this  
Tenth Day of September, 2013

Teresa Stanek Rea  
*Acting Director of the United States Patent and Trademark Office*